(12) United States Patent
Schäfer et al.

(10) Patent No.: US 7,749,417 B2
(45) Date of Patent: Jul. 6, 2010

(54) METHOD AND DEVICE FOR PRODUCING THIN WAFERS FROM A FILM OF ACTIVE INGREDIENTS

(75) Inventors: Wolfgang Schäfer, Ledgewood, NJ (US); Ronald Hackbarth, Koblenz (DE); Detlev Neuland, West Caldwell, NJ (US)

(73) Assignee: LTS Lohmann Therapie-Systeme AG, Andernach (DE)

( * ) Notice: Subject to any disclaimer, the term of this patent is extended or adjusted under 35 U.S.C. 154(b) by 460 days.

(21) Appl. No.: 10/467,894

(22) PCT Filed: Feb. 4, 2002

(86) PCT No.: PCT/EP02/01107

§ 371 (c)(1),
(2), (4) Date: Aug. 13, 2003

(87) PCT Pub. No.: WO02/064123

PCT Pub. Date: Aug. 22, 2002

(65) Prior Publication Data

US 2004/0076799 A1 Apr. 22, 2004

(30) Foreign Application Priority Data

Mar. 5, 2001 (DE) .................. 101 10 494

(51) Int. Cl.
*B28B 11/16* (2006.01)
*B28B 11/12* (2006.01)
*B26D 7/06* (2006.01)

(52) U.S. Cl. .................. 264/157; 264/146; 83/84; 83/86; 83/90; 83/91; 270/52.09; 270/58.07; 242/419.4

(58) Field of Classification Search .................. 83/84
See application file for complete search history.

(56) References Cited

U.S. PATENT DOCUMENTS 2,942,643 A * 6/1960 Pucci et al. .................. 72/338

(Continued)

FOREIGN PATENT DOCUMENTS

DE 949 169 C 9/1956

(Continued)

*Primary Examiner*—Jeffrey Wollschlager
(74) *Attorney, Agent, or Firm*—Birch, Stewart, Kolasch & Birch, LLP

(57) ABSTRACT

The invention relates to a method and a device for producing small, thin sheets from an active-ingredient film (2), in which the latter is produced by casting the film material onto a substrate material or by coating a substrate material, storing it with or without substrate material on a reel, pulling it off the reel and cutting it. It achieves the object of designing a method of this type in such a way that with this method small sheets can be produced as exactly as possible in predetermined sizes. To do this, the active-ingredient film (2) is pulled off automatically, is separated from a substrate material which, if present, and in tensioned form, is fed to a cutting station and is cut, in the feed direction, into long, narrow strips (7) of predeterminable width, and the long strips (7) are brought together in the feed direction and together are fed by a further feed device (10) to a transverse cutter (11), which cuts through the combined long strips (7) at predetermined intervals.

14 Claims, 1 Drawing Sheet

U.S. PATENT DOCUMENTS

| | | | |
|---|---|---|---|
| 3,046,823 A * | 7/1962 | Cole | 83/175 |
| 3,379,390 A * | 4/1968 | Eastcott | 242/421.5 |
| 3,656,513 A | 4/1972 | Evans et al. | |
| 4,008,351 A * | 2/1977 | Inoue et al. | 428/411.1 |
| 4,197,289 A * | 4/1980 | Sturzenegger et al. | 424/443 |
| 4,536,174 A * | 8/1985 | Dreckmann | 493/194 |
| 5,311,801 A * | 5/1994 | Uno | 83/278 |
| 5,816,030 A * | 10/1998 | Carlberg et al. | 53/520 |
| 6,106,930 A | 8/2000 | Ludwig | |
| 6,125,730 A * | 10/2000 | Jacques | 83/408 |
| 6,216,842 B1 * | 4/2001 | Beale et al. | 193/20 |
| 6,659,442 B1 * | 12/2003 | Steinborn et al. | 270/52.09 |
| 7,114,422 B1 * | 10/2006 | Neuland et al. | 83/13 |
| 7,370,563 B2 * | 5/2008 | Neuland et al. | 83/29 |

FOREIGN PATENT DOCUMENTS

| | | |
|---|---|---|
| DE | 199 25 339 A | 12/2000 |
| DE | 199 25 339 A1 | 12/2000 |
| WO | WO9942397 * | 8/1999 |

* cited by examiner

METHOD AND DEVICE FOR PRODUCING THIN WAFERS FROM A FILM OF ACTIVE INGREDIENTS

This application is the national phase under 35 U.S.C. §371 of PCT International Application No. PCT/EP 02/01107 which has an International filing date of Feb. 4, 2002, which designated the United States of America.

BACKGROUND OF TEE INVENTION

1. Field of the Invention

The invention relates to a method and a device for producing small, thin sheet film of one or more active ingredients, in particular for use as a metering and administration form for medicaments.

2. Description of the Related Art

In addition to the known metering forms for medicaments, such as tablets, capsules, droplets or similar administration forms, there is also the "wafer" form of administration. This is a small, thin sheet comprising or containing an active-ingredient film with a predetermined quantity of active ingredient, the thickness and dimensions of which are adapted to the quantity of active ingredient which is to be dispensed. Since the contact area of the wafer is directly related to the metered quantity of the active ingredient, its dimensions must as far as possible correspond to the calculated dimensions and lie within the tolerance range. Therefore, the wafer is complex to produce.

It is known to produce the active-ingredient film by means of casting methods or by a coating method. Usually, the active-ingredient film is cast onto or applied to the film material in some other way, with or without the substrate material, is wound up into reels and is stored. If the active-ingredient film is wound up together with the substrate material, during the subsequent processing of the active-ingredient film to form small, thin sheets, the substrate material is separated from the active-ingredient film and is wound up separately. The thin, flexible active-ingredient film is cut. The actual dimensions produced frequently fail to correspond to the required dimensional tolerances which have been set down in accordance with the metering of the medicament, which is reflected in the active-ingredient tolerance over the area.

SUMMARY OF THE INVENTION

It is an object of the invention to provide a method for producing small, thin sheets from an active-ingredient film that makes it possible to produce small sheets as precisely as possible in predetermined sizes.

In a method, small, thin sheets from an active-ingredient film are produced. A device for carrying out the method is also specified.

DETAILED DESCRIPTION

Figure 1:
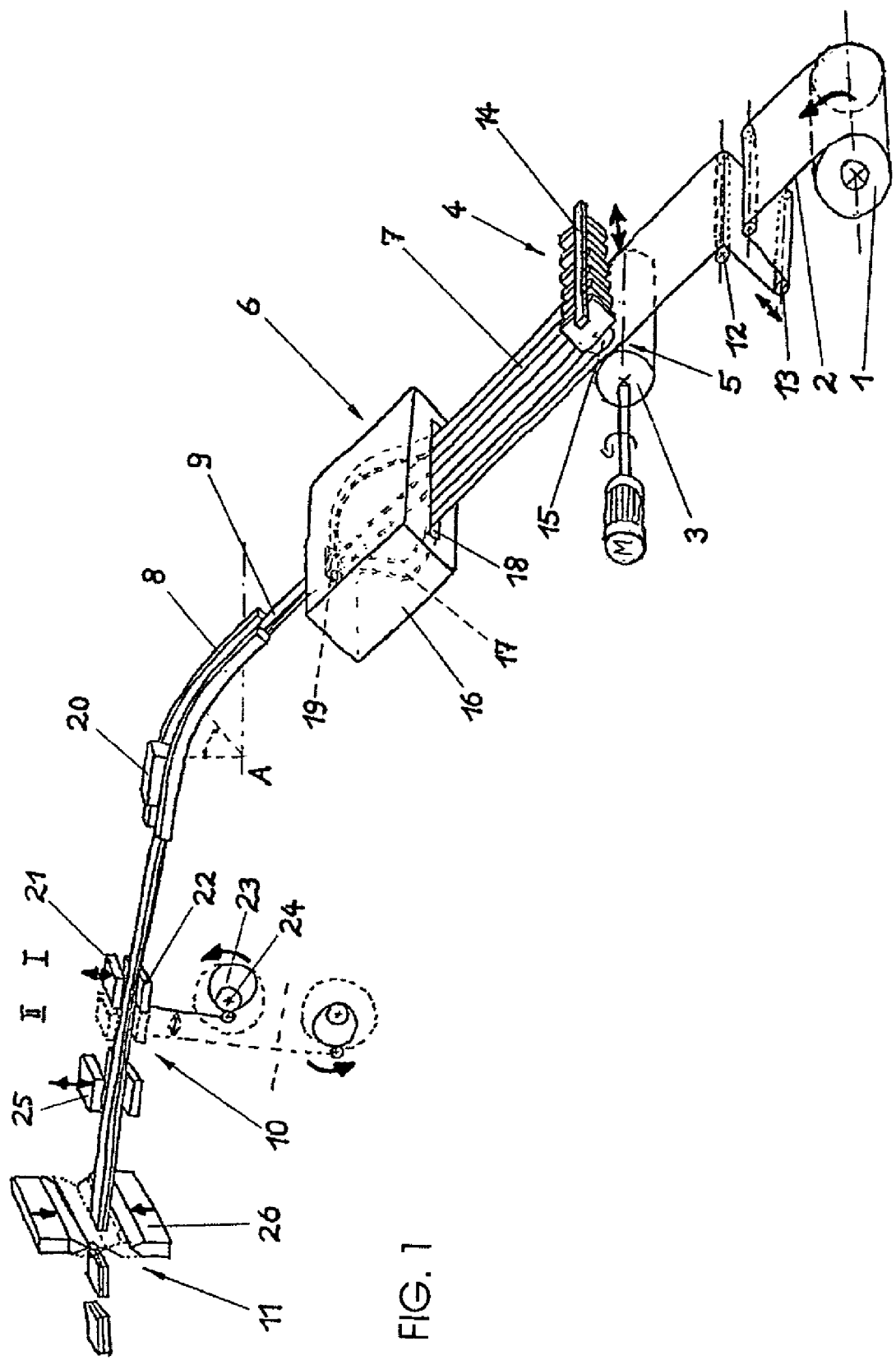
FIG. 1 shows a device for producing small, thin sheets from an active-ingredient film.

Accordingly, in a method which is used to produce small, thin sheets from an active-ingredient film, after this film has been produced by casting the film material onto a substrate material or coating a substrate material and has been stored on a reel with or without substrate material, and in which the active-ingredient film is pulled off the storage reel and cut, the active-ingredient film is automatically pulled off the storage reel, is separated from a substrate material which, if present, and is fed in tensioned form to a strip-cutting station, where it is initially cut into narrow strips of predetermined width in the longitudinal direction, which corresponds to the feed direction. Then, the strips are brought together in the feed direction and are fed as a group, by a further feed device, to a transverse cutter, which cuts through the group at predetermined intervals. The longitudinal and transverse cutting of the active-ingredient film, which operations follow one another physically and in terms of time, produces quadrilateral, in particular rectangular or square, small sheets, the active-ingredient film, at least in terms of its width, being dimensioned in such a way that it is cut into small sheets of predetermined size without any remainder or waste. The size of the small sheets influences the metering. The fact that the active-ingredient film is fed to the strip-cutting station under a prestress facilitates the cutting operation. The fact that the film strips which have been cut in the longitudinal direction are also brought together to form a group of strips likewise facilitates and simplifies the transverse cutting and, moreover, increases the process reliability and dimensional accuracy when producing the small sheets.

Advantageously, the operations of pulling the active-ingredient film of the storage reel and feeding it to the longitudinal cutting station take place continuously, as does the longitudinal cutting into film strips.

To facilitate the longitudinal cutting, a prestress is produced in the active-ingredient film, leading to this film being smoothed and therefore to a precise longitudinal cutting operation. To do this, the active-ingredient film can simply be subjected to a load transversely to the feed direction, in particular by means of a defined weight which, in combination with the width of the active-ingredient film, determines the prestressing.

The cut film strips are preferably brought together to form a stack, so that they rest smoothly on top of one another. The further feeding of the film strips in a simple manner takes place intermittently and can be of reliable design. In order to be fed and pushed towards the transverse cutter, the stack is gripped and clamped by clamping jaws which engage on its upper and lower sides is intermittently pushed to the transverse cutter. To enable this method step also to be carried out with a high process reliability and dimensional accuracy, the stack, upstream of the clamping device, in order to ensure that the strips are arranged precisely on top of one another, in combination with further smoothing and producing a prestress, is guided in a sliding manner so that it maintains its dimensions, in the process being pulled by the feed device and fed to the transverse cutter, relative movements between the individual strips and different lengthening of the material or strips being suppressed.

A device for carrying out the method as a holding device for a storage reel with the film material, a feed roller which is driven by electric motor for pulling the active-ingredient film off the storage reel at least in its width, a strip-cutting device, formed by the feed roller and a cutting-blade device which interacts therewith, a device for bringing together and stacking the said cut film strips (stacking device) and a further feed device therefor and a transverse cutting device. Means for smoothing the stack of strips and, in conjunction with the further feed device, means for producing a prestress are arranged between the stacking device and the further feed device.

Two guide rollers for the active-ingredient film, between which a dancer roll rests on the active-ingredient film in order to produce a stress in the latter, are arranged in the feed region between the storage reel and the feed roller, parallel to these components. The cutting-blade device has round cutting discs which can rotate next to and at a distance from one another, are held parallel to the feed direction next to and at a distance from one another on a holding device and are pressed onto the active-ingredient film which is advanced on the feed roller. The distance between the cutting discs is adjustable.

A combining and stacking device for the cut fed strips forms part of the overall device. A device of this type is described in DE 199 25 339 A1.

The film strips which are to be brought together and stacked are fed intermittently by means of a gripper feed system, which intermittently grips the stack and exerts a tensile force on it and which also pushes the stack to the transverse cutter.

A U-shaped three-sided slideway, in which the stack is moved by the gripper feed system, is arranged between the stacking device and the gripper feed system. Weights which are held in a stationary position but so that they can move in vertical guides and rest on the moving stack, thus smoothing the latter during its feed movement, are arranged on this slideway. The slideway is bent convexly about an axis which lies transversely with respect to the feed direction, as seen in plan view of the stack, so that a defined prestress is produced in the stack, which has to be overcome by the gripper feed system as a precisely defined resistance. The feed section of the gripper feed system determines the length of the small sheets.

The gripper feed system is provided with two clamping jaws, which are coupled to a drive by means of a conveyor cam and, with respect to the feed direction, are moved backward and forward, the clamping jaws, for the purpose of the forward movement, clamping the stack between them at a distance from that end of the stack is on the side of the transverse cutter and pull it off the slideway, counter to the resistance produced on the slideway, at the same time pushing the stack section of defined length which is situated in front of the gripper feed system, as seen in the feed direction, into the transverse cutter. The conveyor cam is eccentrically mounted, and the clamping jaws are in continuous engagement therewith, so that continuous rotation of the conveyor cam is converted into a defined forward and backward translational movement of the clamping jaws. A change in the dimensions or the shape of the conveyor leads to a change in the magnitude of the translational movement and therefore in the feed, with the result that the cut length of the stack and therefore the length of the small sheets can be predetermined.

The invention is explained below with reference to an exemplary embodiment. The associated drawing shows a device for producing small, thin sheets from an active-ingredient film, partially diagrammatically.

The device has a storage area 1 with a stock of active-ingredient film 2 of a thickness of approximately 0.05 mm, in a holding means which is not shown, a motor-driven (M) vacuum roller 3 and a feed roller for pulling the active-ingredient film 2 off the storage reel 1, a longitudinal cutting device 5, which is formed with the vacuum roller 3 and a cutting-blade device 4 which interacts with the latter, a stacking device 6 for the cut long strips 7, a three-sided slideway 8, which is U-shaped in cross section, for the stack 9 which is formed from the long strips 7, a gripper feed system 10 and a transverse cutting device 11 for the stack 9. Two guide rollers 12 for the active-ingredient film 2 are arranged between the storage reel 1 and the longitudinal cutting device 5, parallel to the storage reel 1, and a dancer roller 13, which acts on this active-ingredient film 2 for tautening this film, is arranged between these guide rollers 12.

The cutting-blade device 4 comprises a holding device 14, which is not shown in more detail, and rotatable round cutting disks 15, which are held next to one another on the holding device at an adjustable distance from one another, are oriented parallel to the feed direction of the active-ingredient film 2, are pressed onto the active-ingredient film 2 and cut the latter in the longitudinal direction, in accordance with their arrangement, as it is advanced by the vacuum roller 3. In the exemplary embodiment, the distance between the cutting disks 15 is 20 mm.

In a stacking block 16, the stacking device 6 has, for each long strip 7, a vacuum conveyor channel 17 which is coupled to a vacuum device (not shown) and, together with the other vacuum conveyor channels 17, arranged next to one another, is connected to a common entry 18. In the stacking block 16, the channels 17 run in such a way that they are brought together above one another at a common exit 19.

The stacking device 6 is followed by the three-sided slideway 8, which is bent around an axis A, which is arranged transversely to the feed direction or parallel to the axis of the vacuum roller 3 of the rollers 1, 12 and 13, and receives the stack 9 so as to guide its sides, the width between the side walls of the three-sided slideway 8 substantially corresponding to the width of the stack 9. In a vertical guide, which is not shown, a weight 20 of 120 g from the stack 9, resting on the stack and thus compressing and smoothing the latter.

As seen in the feed direction, the gripper feed system 10 is arranged downstream of the three-sided slideway 8, which gripper feed system has two clamping jaws 21 and 22, which are arranged one above the other, for intermittently gripping the stack 9 and are coupled to a drive 4 by means of an exchangeable, eccentric conveyor cam 23. These components (23, 24) move the clamping jaws 21, 22 forward and backward, with respect to the feed direction, during which movement the clamping jaws 21 and 22 pick up the stack 9 in their rear dead center position I and release it again at their front dead center position II.

The gripper feed system 10 is followed by guide jaws 25, between which the stack 9 slides toward the transverse cutting device 11, in which it is cut transversely between two cutting blades 26. The predeterminable length of the stack section is 25 mm, resulting in a wafer size of 20×25 mm.

The wafers which have been produced are then packaged in dispensers, blister packs or tubular bags on a packaging machine.

The invention claimed is:

1. A method for producing small, thin sheets from an active-ingredient film, in which the latter is produced by casting the film material onto a substrate material or by coating a substrate material, comprising the following steps:
   storing the film with or without the substrate material on a reel;
   pulling the film off the reel;
   separating the substrate material, if present, from the film;
   feeding the film in tensioned form to a cutting station;
   cutting the film in the feed direction, into long, narrow strips of predeterminable width;
   bringing the long strips together in the feed direction;
   arranging the long strips on top of one another in the form of a stack of individual strips;
   feeding the stack of individual strips by a further feed device to a transverse cutter in that the stack of individual strips is pulled over a slideway by the further feed device and the stack is smoothed in this step, said slideway being three-sided and U-shaped in cross section, and being bent convexly around an axis which lies transversely with respect to the feed direction so as to produce prestress in the stack, with the width between the side walls of the three-sided slideway substantially corresponding to the width of the stack, wherein the feeding of the stack of individual strips to the transverse cutter causes the stack of strips to slide between a pair of guide jaws, one guide jaw of said pair of guide jaws being arranged above said stack of individual strips, and the respective other guide jaw of said pair of guide jaws being arranged below said stack of individual strips; and cutting through the stack of individual strips at predetermined intervals with the transverse cutter.

2. The method as claimed in claim 1, wherein the active-ingredient film is pulled off the storage reel and is fed continuously to the cutting station by means of a driven roller, over which the active-ingredient film is guided and on which this film is cut into long strips.

3. The method as claimed in claim 1, wherein the stack is intermittently pushed into the transverse cutter.

4. The method as claimed in claim 1, wherein the stack of individual strips is smoothed by means of at least one weight which is arranged in vertical guides at a stationary position on said slideway and which can move vertically in said vertical guides and rest on the moving stack, thus prestressing and smoothing the stack while it is pulled over the slideway and while it slides underneath said weight.

5. The method as claimed in claim 4, wherein a width of a portion of the weight contacting the stack substantially corresponds to the width between the side walls of the three-sided slideway.

6. The method as claimed in claim 1, wherein the step of feeding the stack includes intermittently gripping the stack by a gripper feed system after receiving the stack from the slideway and feeding the stack to the transverse cutter.

7. A method for producing small, thin sheets from an active-ingredient film, in which the latter is produced by casting the film material onto a substrate material or by coating a substrate material, comprising the following steps:
  storing the film with or without the substrate material on a reel;
  pulling the film off the reel automatically;
  separating the substrate material, if present, from the film;
  feeding the film in tensioned form to a cutting station;
  cutting the film in the feed direction, into long, narrow strips of predeterminable width;
  bringing the long strips together in the feed direction;
  arranging the long strips on top of one another in the form of a stack of individual strips;
  feeding the stack of individual strips by a further feed device to a transverse cutter in that the stack of individual strips is pulled over an U-shaped slideway by the further feed device, and the stack is smoothed by means of at least one weight which is arranged in vertical guides at a stationary position on said slideway, and which can move vertically in said vertical guides and rest on the moving stack, thus prestressing and smoothing the stack while it is pulled over the slideway and while it slides underneath said weight,
  wherein feeding the stack of individual strips to the transverse cutter causes the stack of strips to slide between a pair of guide jaws to said transverse cutter, one guide jaw of said pair of guide jaws being arranged above said stack of individual strips, and the respective other guide jaw of said pair of guide jaws being arranged below said stack of individual strips; and
  cutting through the stack of individual strips at predetermined intervals with the transverse cutter.

8. The method as claimed in claim 7, wherein the step of feeding the stack includes intermittently gripping the stack by a gripper feed system after receiving the stack from the slideway and feeding the stack to the transverse cutter.

9. The method as claimed in claim 7, wherein a width of a portion of the weight contacting the stack substantially corresponds to the width between the side walls of the three-sided slideway.

10. A method for producing small, thin sheets from an active-ingredient film, in which the latter is produced by casting the film material onto a substrate material or by coating a substrate material, comprising the following steps:
  storing the film with or without the substrate material on a reel;
  pulling the film off the reel;
  separating the substrate material, if present, from the film;
  feeding the film in tensioned form to a cutting station;
  cutting the film in the feed direction, into long, narrow strips of predeterminable width;
  bringing the long strips together in the feed direction;
  arranging the long strips on top of one another in the form of a stack of individual strips;
  feeding the stack of individual strips by a further feed device to a transverse cutter in that the stack of individual strips is pulled over a slideway by the further feed device and the stack is smoothed in this step, said slideway being three-sided and U-shaped in cross-section, and being bent convexly around an axis which lies transversely with respect to the feed direction, so as to produce prestress in the stack, with the width between the side walls of the three-sided slideway substantially corresponding to the width of the stack; and
  cutting through the stack of individual strips at predetermined intervals with the transverse cutter,
  wherein the step of feeding the stack includes intermittently gripping the stack by a gripper feed system after receiving the stack from the slideway, and feeding the stack to the transverse cutter, and wherein said gripper feed system has two clamping jaws for the stack, which are coupled to a drive by means of an exchangeable eccentric conveyor cam which moves the clamping jaws backward and forward with respect to the feed direction, and wherein the clamping jaws clamp the stack securely during its forward movement.

11. A method for producing small, thin sheets from an active-ingredient film, in which the latter is produced by casting the film material onto a substrate material or by coating a substrate material, comprising the following steps:
  storing the film with or without the substrate material on a reel;
  pulling the film off the reel automatically;
  separating the substrate material, if present, from the film;
  feeding the film in tensioned form to a cutting station;
  cutting the film in the feed direction, into long, narrow strips of predeterminable width;
  bringing the long strips together in the feed direction;
  arranging the long strips on top of one another in the form of a stack of individual strips;
  feeding the stack of individual strips by a further feed device to a transverse cutter in that the stack of individual strips is pulled over an U-shaped slideway by the further feed device, and the stack is smoothed by means of at least one weight which is arranged in vertical guides at a stationary position on said slideway, and which can move vertically in said vertical guides and rest on the moving stack, thus prestressing and smoothing the stack while it is pulled over the slideway and while it slides underneath said weight; and cutting through the stack of individual strips at predetermined intervals with the transverse cutter, wherein the step of feeding the stack includes intermittently gripping the stack by a gripper feed system after receiving the stack from the slideway, and feeding the stack to the transverse cutter, and wherein said gripper feed system has two clamping jaws for the stack, which are coupled to a drive by means of an exchangeable eccentric conveyor cam which moves the clamping jaws backward and forward with respect to the feed direction, and wherein the clamping jaws clamp the stack securely during its forward movement.

12. The method as claimed in claim 11, wherein said weight is non-rotatable.

13. A method for producing small, thin sheets from an active-ingredient film, in which the latter is produced by casting the film material onto a substrate material or by coating a substrate material, comprising the following steps:

storing the film with or without the substrate material on a reel;

pulling the film off the reel;

separating the substrate material, if present, from the film;

feeding the film in tensioned form to a cutting station;

cutting the film in the feed direction, into long, narrow strips of predeterminable width;

bringing the long strips together in the feed direction;

arranging the long strips on top of one another in the form of a stack of individual strips;

feeding the stack of individual strips by a further feed device to a transverse cutter in that the stack of individual strips is pulled over a slideway by the further feed device and the stack is smoothed in this step, said slideway being three-sided and U-shaped in cross-section, and being bent convexly around an axis which lies transversely with respect to the feed direction, so as to produce prestress in the stack, with the width between the side walls of the three-sided slideway substantially corresponding to the width of the stack; and cutting through the stack of individual strips at predetermined intervals with the transverse cutter, wherein the step of feeding the stack includes intermittently gripping the stack by a gripper feed system after receiving the stack from the slideway, and feeding the stack to the transverse cutter, and wherein said gripper feed system has two clamping jaws for the stack, which are coupled to a drive by means of an eccentric conveyor cam which moves the clamping jaws backward and forward with respect to the feed direction, and wherein the clamping jaws clamp the stack securely during its forward movement.

14. A method for producing small, thin sheets from an active-ingredient film, in which the latter is produced by casting the film material onto a substrate material or by coating a substrate material, comprising the following steps:

storing the film with or without the substrate material on a reel;

pulling the film off the reel automatically;

separating the substrate material, if present, from the film;

feeding the film in tensioned form to a cutting station;

cutting the film in the feed direction, into long, narrow strips of predeterminable width;

bringing the long strips together in the feed direction;

arranging the long strips on top of one another in the form of a stack of individual strips;

feeding the stack of individual strips by a further feed device to a transverse cutter in that the stack of individual strips is pulled over an U-shaped slideway by the further feed device, and the stack is smoothed by means of at least one weight which is arranged in vertical guides at a stationary position on said slideway, and which can move vertically in said vertical guides and rest on the moving stack, thus prestressing and smoothing the stack while it is pulled over the slideway and while it slides underneath said weight; and cutting through the stack of individual strips at predetermined intervals with the transverse cutter, wherein the step of feeding the stack includes intermittently gripping the stack by a gripper feed system after receiving the stack from the slideway, and feeding the stack to the transverse cutter, and wherein said gripper feed system has two clamping jaws for the stack, which are coupled to a drive by means of an eccentric conveyor cam which moves the clamping jaws backward and forward with respect to the feed direction, and wherein the clamping jaws clamp the stack securely during its forward movement.

* * * * *

UNITED STATES PATENT AND TRADEMARK OFFICE
CERTIFICATE OF CORRECTION

PATENT NO. : 7,749,417 B2  Page 1 of 1
APPLICATION NO. : 10/467894
DATED : July 6, 2010
INVENTOR(S) : Schafer et al.

It is certified that error appears in the above-identified patent and that said Letters Patent is hereby corrected as shown below:

ON THE TITLE PAGE:

Insert the following domestic application information:

-- Related U.S. Application Data

(60) Provisional Application No. 60/268,805, filed on Feb. 14, 2001 --.

Signed and Sealed this
Fourteenth Day of June, 2011

David J. Kappos
*Director of the United States Patent and Trademark Office*